US00PP22414P2

(12) United States Plant Patent
Ren

(10) Patent No.: US PP22,414 P2
(45) Date of Patent: Dec. 27, 2011

(54) *PETUNIA* PLANT NAMED 'BALPEPIN'

(50) Latin Name: *Petunia×hybrida*
Varietal Denomination: Balpepin

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/924,299

(22) Filed: Sep. 24, 2010

(51) Int. Cl.
*A01H 5/00* (2006.01)

(52) U.S. Cl. ..... Plt./356.13
(58) Field of Classification Search ..... Plt./356.13, Plt./356
See application file for complete search history.

(56) References Cited

U.S. PATENT DOCUMENTS 7,642,436 B2 1/2010 Riebel et al.

*Primary Examiner* — Annette Para
(74) *Attorney, Agent, or Firm* — Audrey Charles

(57) ABSTRACT

A new and distinct cultivar of *Petunia* plant named 'Balpepin', characterized by its deep velvety-purple and cream bicolored flowers, medium green-colored foliage, and moderately vigorous, semi-upright growth habit, is disclosed.

1 Drawing Sheet

Latin name of the genus and species of plant claimed: *Petunia×hybrida.*

Variety denomination: 'Balpepin'.

BACKGROUND OF THE INVENTION

The present invention relates to a new and distinct cultivar of *Petunia* plant botanically known as *Petunia×hybrida* and hereinafter referred to by the cultivar name 'Balpepin'.

The new cultivar originated in a controlled breeding program in Elburn, Ill. during March 2006. The objective of the breeding program was the development of *Petunia* cultivars with unique and attractive flower coloration.

The new *Petunia* cultivar is the result of cross-pollination. The female (seed) parent of the new cultivar is the proprietary *Petunia×hybrida* breeding selection designated 2445-1, U.S. Pat. No 7,642,436, characterized by its dark velvet purple and yellow bicolored flowers, medium green-colored foliage, and moderately vigorous, semi-upright growth habit. The male (pollen) parent of the new cultivar is the proprietary *Petunia×hybrida* breeding selection designated 2329-4-3, not patented, characterized by its medium burgundy and white bicolored flowers, medium green-colored foliage, and moderately vigorous, compact growth habit. The new cultivar was discovered and selected as a single flowering plant within the progeny of the above stated cross-pollination during February 2007 in a controlled environment at Elburn, Ill.

Asexual reproduction of the new cultivar by terminal stem cuttings since February 2007 at Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balpepin' as a new and distinct cultivar of *Petunia* plant:

1. Deep velvety-purple and cream bicolored flowers;
2. Medium green-colored foliage; and
3. Moderately vigorous, semi-upright growth habit.

Plants of the new cultivar differ from plants of the female and male parents primarily in flower color.

Of the many commercially available *Petunia* cultivars, the most similar in comparison to the new cultivar is Cascadias Bicolor Purple, not patented. However, in side by side comparisons, plants of the new cultivar differ from plants of Cascadias Bicolor Purple in at least the following characteristics:

1. Plants of the new cultivar have a flower color different from plants of Cascadias Bicolor Purple; and
2. Plants of the new cultivar have larger flowers, as measured by corolla diameter, than plants of Cascadias Bicolor Purple.

In addition, plants of the new cultivar are similar to 'Balpevac', co-pending U.S. Plant patent application. However, in side by side comparisons in West Chicago, Ill., plants of the new cultivar differ from plants of 'Balpevac' in at least the following characteristics:

1. Plants of the new cultivar have a flower color different from plants of 'Balpevac';
2. Plants of the new cultivar have larger flowers, as measured by corolla diameter, than plants of 'Balpevac'; and
3. Plants of the new cultivar have fewer main branches than plants of 'Balpevac'.

Further, plants of the new cultivar are similar to 'Balpephan', co-pending U.S. Plant patent application. However, in side by side comparisons in West Chicago, Ill., plants of the new cultivar differ from plants of 'Balpephan' in at least the following characteristics:

1. Plants of the new cultivar have a flower color different from plants of 'Balpephan'; and
2. Plants of the new cultivar have larger flowers, as measured by corolla diameter, than plants of 'Balpephan'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balpepin'. The plants were grown in 4-inch pots for 6 weeks in a greenhouse at West Chicago, Ill.

DETAILED BOTANICAL DESCRIPTION

Figure 1:
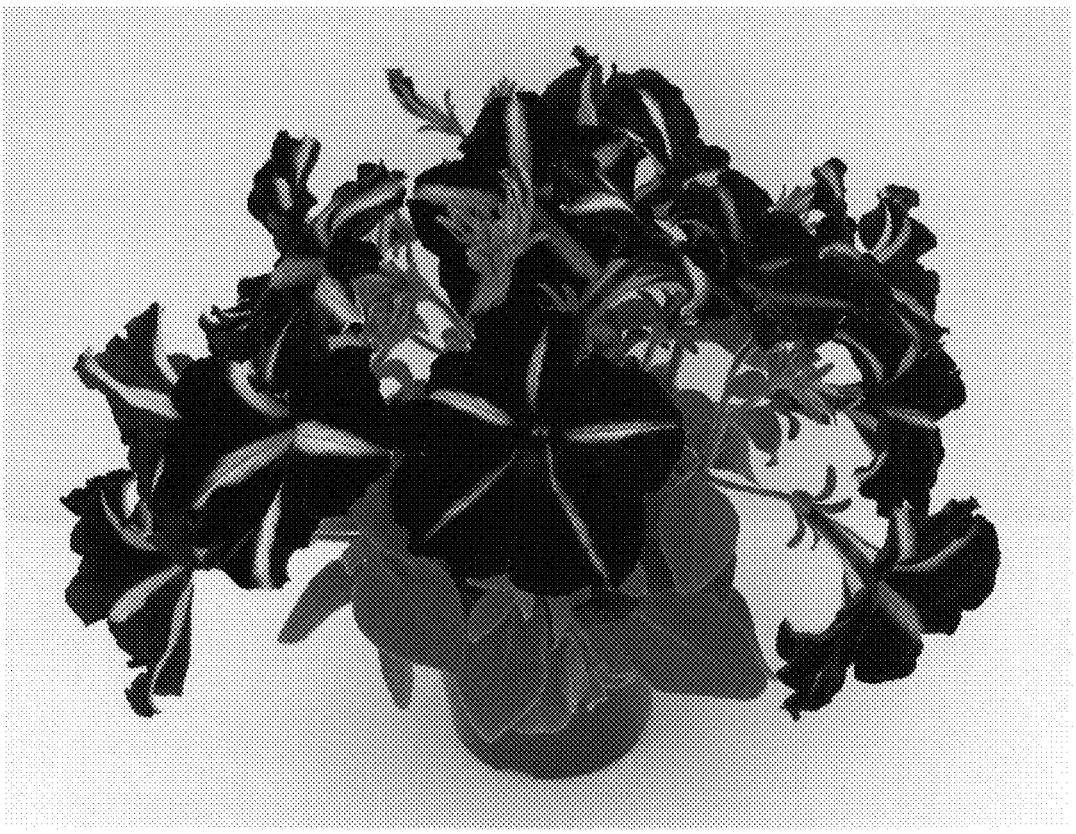
FIG. 1 illustrates a side view of the overall growth and flowering habit of 'Balpepin'.
Figure 2:
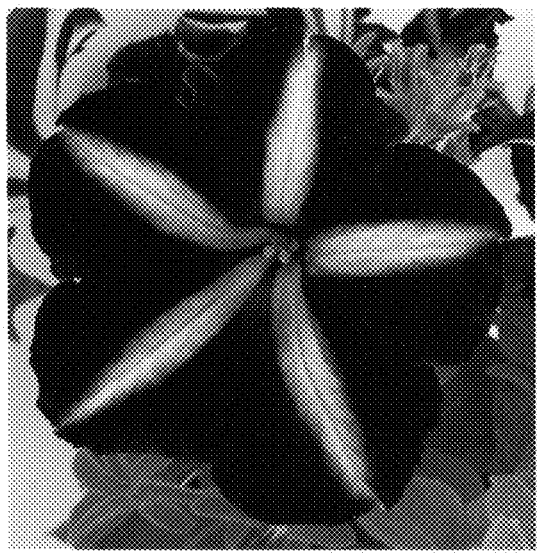
FIG. 2 illustrates a close-up view of an individual flower of 'Balpepin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in May 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Petunia×hybrida* cultivar Balpepin.

Parentage:

*Female parent.*—Proprietary *Petunia×hybrida* breeding selection designated 2445-1, U.S. Pat. No. 7,642,436.

*Male parent.*—Proprietary *Petunia×hybrida* breeding selection designated 2329-4-3, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, semi-upright.

*Size.*—Height from soil level to top of plant plane: Approximately 18.7 cm. Width: Approximately 24.8 cm.

*Branching habit.*—Freely branching, pinching improves basal branching. Quantity of main branches per plant: Approximately 6.

*Branch.*—Strength: Moderate. Length: Approximately 14.7 cm. Diameter: Approximately 5.0 mm. Length of central internode: Approximately 1.6 cm. Texture: Densely glandular pubescent with a mixture of long and short length hairs. Gland color: Colorless. Color of young stem: 144A. Color of mature stem: 144A.

Foliage description:

*General description.*—Quantity of leaves per main branch: Approximately 9. Fragrance: Slight. Form: Simple. Arrangement on flowering stem: Opposite.

*Leaves.*—Aspect: Perpendicular to acute angle to stem. Shape: Ovate. Margin: Entire, slightly wavy. Apex: Broadly acute. Base: Attenuate. Venation pattern: Pinnate. Length of mature leaf: Approximately 5.3 cm. Width of mature leaf: Approximately 3.4 cm. Texture of upper and lower surfaces: Moderately glandular pubescent. Gland color: Colorless. Color of upper surface of young foliage: 137B with venation of 144B. Color of lower surface of young and mature foliage: 138B with venation of 144B. Color of upper surface of mature foliage: 137A with venation of 144B.

*Petiole.*—Length: Approximately 7.0 mm. Width: Approximately 3.0 mm. Texture: Densely glandular pubescent with a mixture of long and short length hairs. Gland color: Colorless. Color: 144B.

Flowering description:

*Flowering habit.*—'Balpepin' is freely flowering under outdoor growing conditions with substantially continuous blooming from spring through autumn and year-round in greenhouse environment.

*Lastingness of individual flower on the plant.*—Approximately 10 to 12 days.

Flower description:

*General description.*—Type: Simple, salverform. Quantity per plant: Approximately 16. Fragrance: Slight.

*Bud.*—Rate of opening: Generally takes 2 to 3 days for bud to progress from first color to fully open flower. Quantity per plant: Approximately 4.

*Bud just before opening.*—Shape: Oblong. Length: Approximately 3.4 cm. Diameter at apex: Approximately 1.0 cm. Diameter at base: Approximately 3.0 mm. Texture: Densely pubescent. Color of petals and tube: N186A with stripes and venation of 154B.

*Corolla.*—Diameter: Approximately 8.0 cm.

*Petals.*—Quantity: 5, fused to form a tube. Shape: Obovate. Appearance: Velvety. Margin: Entire, slightly wavy. Apex: Rounded to broadly acute. Length from tube: Approximately 3.6 cm. Length of free portion: Approximately 1.8 cm. Width: Approximately 4.0 cm. Texture of upper surface: Glabrous. Texture of lower surface: Sparsely glandular pubescent. Color of upper surface when first and fully open: Closest to N186A, midviens surrounded by a broad stripe of 155A edged with N81A to N81B. Color of lower surface when first and fully open: N186B, midveins surrounded by a broad stripe of 154C.

*Corolla tube.*—Length: Approximately 3.1 cm. Diameter at distal end: Approximately 9.0 mm. Diameter at proximal end: Approximately 3.0 mm. Texture of inner surface: Glabrous. Texture of outer surface: Densely glandular pubescent. Gland color: Colorless. Color of inner surface: Closest to N186A, midviens surrounded by a broad stripe of 155A. Color of outer surface: N186B, midveins surrounded by a broad stripe of 154C.

*Sepals.*—Quantity per flower: 5, fused at base. Shape: Linear. Apex: Broadly acute. Length: Approximately 1.5 cm. Width: Approximately 5.0 mm. Texture of upper surface: Densely glandular pubescent. Texture of lower surface: Densely glandular pubescent. Color of upper surface: 137A transitioning to 144A at base. Color of lower surface: 137C transitioning to 144A at base.

*Peduncle.*—Strength: Strong. Aspect: Acute angle to stem. Length: Approximately 3.0 cm. Diameter: Approximately 2.0 mm. Texture: Densely glandular pubescent with a mixture of long and short length hairs. Gland color: Colorless. Color: 144A, often with an overlay of 187A.

*Reproductive organs.*—Androecium: Stamen quantity: 5, basifixed. Stamen length: Approximately 2.3 cm. Filament length of fixed portion: Approximately 1.0 cm. Filament color: 155D with streaks of N82A. Anther shape: Bilobed. Anther length: Approximately 1.0 mm. Anther color: N155A with speckles of N82A. Pollen amount: Abundant. Pollen color: N155A. Gynoecium: Pistil quantity: 1 per flower. Pistil length: Approximately 2.5 cm. Stigma shape: Funnel. Stigma length: Approximately 2.0 mm. Stigma color: 144A with an overlay of N82A at base. Style length: Approximately 2.0 cm. Style color: 145B. Ovary length: Approximately 3.0 mm. Ovary color: 144A with speckles of N186A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balpepin', substantially as herein shown and described.

* * * * *